US008716325B2

(12) United States Patent
Cavalla

(10) Patent No.: US 8,716,325 B2
(45) Date of Patent: May 6, 2014

(54) TREATMENT OF CACHEXIA

(75) Inventor: David Cavalla, Cambridge (GB)

(73) Assignee: PsiOxus Therapeutics Limited, London (GB)

(*) Notice: Subject to any disclaimer, the term of this patent is extended or adjusted under 35 U.S.C. 154(b) by 751 days.

(21) Appl. No.: 12/312,756

(22) PCT Filed: Dec. 5, 2007

(86) PCT No.: PCT/GB2007/004644
§ 371 (c)(1),
(2), (4) Date: Sep. 2, 2009

(87) PCT Pub. No.: WO2008/068477
PCT Pub. Date: Jun. 12, 2008

(65) Prior Publication Data
US 2010/0292270 A1 Nov. 18, 2010

(30) Foreign Application Priority Data
Dec. 5, 2006 (GB) .................................. 0624282.0

(51) Int. Cl.
A61K 31/404 (2006.01)
A61K 31/4704 (2006.01)
A61K 31/38 (2006.01)
A61K 31/135 (2006.01)
A61K 31/138 (2006.01)

(52) U.S. Cl.
USPC ............ 514/415; 514/312; 514/432; 514/652

(58) Field of Classification Search
None
See application file for complete search history.

(56) References Cited

U.S. PATENT DOCUMENTS

| 5,324,738 | A | 6/1994 | Dinan et al. |
| 5,403,848 | A | 4/1995 | Dinan et al. |
| 5,541,188 | A | 7/1996 | Maltin |
| 6,545,040 | B1 | 4/2003 | Xhonneux et al. |
| 6,855,729 | B2 | 2/2005 | Dinan et al. |
| 7,354,941 | B2 | 4/2008 | Marfat et al. |
| 2007/0149465 | A1 | 6/2007 | Kenley et al. |

FOREIGN PATENT DOCUMENTS

| EP | 0334429 B1 | 11/1992 |
| EP | 1793818 A2 | 9/2006 |
| EP | 1809104 A2 | 10/2006 |
| EP | 1865779 A2 | 4/2007 |
| EP | 2081569 A2 | 10/2008 |
| EP | 1990049 A2 | 11/2008 |
| EP | 1991270 A2 | 11/2008 |
| EP | 2001495 A2 | 12/2008 |
| WO | WO 00/21509 | 4/2000 |
| WO | WO 2006/030306 A2 | 3/2006 |
| WO | WO 2006/102476 A2 | 9/2006 |
| WO | WO 2008/129308 A2 | 10/2008 |
| WO | WO 2009/111648 A1 | 9/2009 |

OTHER PUBLICATIONS

Nagatomo et al., "Pharmacological characteristics of the long-acting beta-blocker bopindolol," Nihon Yakurigaku Zasshi, Jan. 1997; 109(1): 1-12—abstract only.*
Hryniewicz et al., Partial Reversal of Cachexia by β-adrenergic Receptor Blocker Therapy in Patients with Chronic Heart Failure, J. of Cardiac Failure, 2003, vol. 9, No. 6, pp. 464-468.*
Aellig, W.H., "Pindolol-A β-Adrenoceptor Blocking Drug with Partial Agonist Activity: Clinical Pharmacological Considerations," Br. J. Clin. Pharmac. 13:187S-192S (1982).
Doggrell, S.A., "Effects of (±)- (+)- and (−)-Metoprolol, (±)- (+)- and (−)-Pindolol, (±)-Mepindolol and (±)-Bopindolol on the Rat Left Atria and Portal Vein," Gen. Pharmac. 22(6):1169-1177 (1991).
Hsyu, P.-H., et al. "Stereoselective Renal Clearance of Pindolol in Humans," J. Clin. Invest. 76:1720-1726 (1985).
Walle, T., et al., "Stereoselective Delivery and Actions of Beta Receptor Antagonists," Biochemical Pharmacology 37(1):115-124 (1988).
Walter, M., et al., "Stimulant and Blocking Effects of Optical Isomers of Pindolol on the Sinoatrial Node and Trachea of Guinea Pig. Role of β-adrenoceptor Subtypes in the Dissociation Between Blockade and Stimulation," Naunyn-Schmiedeberg's Arch Pharmacol 327:159-175 (1984). (Abstract).
Yan, H., et al., "Differential Tissue Distribution of the Enantiomers of Racemic Pindolol in the Rat," European Neuropsychopharmacology 10:59-62 (1999).
Notification of Transmittal of The International Search Report and the Written Opinion of the International Searching Authority, or the Declaration, PCT/GB2007/004644, mailed Mar. 7, 2008.
Alexander & Wood, J. Pharm. Pharmacol. 39: 664-666 (Feb. 10, 1987).
Dewys, et al., Eastern Cooperative Oncology Group, Am. J. Med. 69: 491-497 (Oct. 1980).
Fearon, et al., Am. J. Clin. Nutr 83: 1345-1350 (Feb. 15, 2006).
Ko, et al., JAMA 288(3): 351-357 (Jul. 17, 2002).
Morley, et al., Am. J. Clin. Nutr. 83: 735-743 (2006).
Sprouse & Aghajanian, Eur. J. Pharmacol. 128(3): 295-298 (Jul. 22, 1986).
Steinborn & Anker, Basic Appl. Myol. 13(4): 191-201 (2003).
Stoschitzky, et al., J. Cardiovasc Pharmacol, 25(2): 268-272 (1995).
Uomo, et al., J. Pancreas (Online) 7(2): 157-162 (Mar. 2006).
Szabó, "Clinical Experiences with Beta Adrenergic Blocking Therapy on Burned Patients," Scand J. Plast Reconstr Surg, 1979, vol. 13, pp. 211-215.
Cleophas & Van De Meulen, "Beta-blockers: ancillary properties important after all?" East. J. Med. 4, 1-5, 1999.
Helfand et al., "Drug Class Review—Beta Adrenergic Blockers," Final Report Update 4, 1-616, Jul. 2009.

(Continued)

Primary Examiner — Sreeni Padmanabhan
Assistant Examiner — Jody Karol
(74) Attorney, Agent, or Firm — Banner & Witcoff, Ltd.

(57) ABSTRACT

The present invention provides a means for prevention and treatment of cachexia and other chronic illnesses including but not limited to the promotion of weight gain, reduction or prevention of weight loss by administration of a substance that both reduces the sensitivity of beta-adrenergic receptors and of 5-HT1a receptors. (S)-pindolol, (S)-propranolol, tertatolol or bopindolol are preferred for this purpose.

16 Claims, No Drawings

(56) References Cited

OTHER PUBLICATIONS

Rabiner et al., "β-blocker Binding to Human 5-HT$_{1A}$ Receptors in vivo and in vitro: Implications for Antidepressant Therapy," Neuropsychopharmacology 23, 285-93, 2000.

Soriano et al., "Increased Survival With β-blockers: Importance of Ancillary Properties," *Progr. Cardiovascular Diseases 34*, 445-56, 1997.

* cited by examiner

TREATMENT OF CACHEXIA

RELATED APPLICATIONS

This application is the U.S. National Stage of International Application No. PCT/GB2007/004644, filed Dec. 5, 2007, which designates the U.S., published in English, and claims priority under 35 U.S.C. §§119 or 365(c) to Great Britain Application No. 0624282.0, filed Dec. 5, 2006.

FIELD OF THE INVENTION

The present invention lies in the field of compounds or methods for the treatment of cachexia.

Cachexia occurs in many end-stage illnesses such as cancer, heart failure, chronic obstructive pulmonary diseases (COPD), liver failure, kidney failure, stroke, rheumatoid arthritis, severe burn injury and HIV/AIDS. It also occurs in ageing.

In severe COPD, heart failure, liver failure and kidney failure, approximately 30% of patients have cachexia; in heart failure and AIDS, the proportion is nearer to 10%.

Cachexia occurs in approximately 50% of all cancer patients, and may be either as a direct result of the disease or as a consequence of its treatment. It is considered that cachexia can interfere with radio- or chemotherapy and that its management can improve outcomes and provide a sense of well-being for patients and their families.

Cachexia has been described as a debilitating state of involuntary weight loss (Uorno et al, J Pancreas (Online) 2006; 7 (2): 157-162), though there is as yet no formal agreed definition. Fearon et al (Am J Clin Nutr 2006; 83: 1345-50) states "Patients with advanced cachexia are characterized by anorexia, early satiety, severe weight loss, weakness, anemia, and edema . . . . In relation to the approval of novel therapeutics for cachexia, regulatory authorities suggest it is important not only to show efficacy for improved nutritional status such as lean body mass (LBM) but also functional status such as performance status . . . . Poor physical function in cachexia may relate to many factors, including loss of body mass, reduced substrate supply (food intake), or reduced volitional effort (fatigue or depression); all of which have been related, at least in part, to the effects of systemic inflammation."

Although often associated with a chronic illness, cachexia is not always so associated, and is also present in the absence of an underlying disease. When present, treatment of the underlying disease will not necessarily treat the cachexia. Cachexia itself is of prognostic importance in the context of cancer (Dewys W D et al. Eastern Cooperative Oncology Group. Am J Med 1980; 69: 491-7) and heart failure (Steinborn C, Anker S D, Basic Appl Myol 13 (4): 191-201, 2003); hence, treatment of cachexia independently of the underlying disease is of medical benefit. Cachexia is not effectively treated with nutritional intervention, and so is distinct from eating disorders such as anorexia. Cachexia also typically involves disproportionate loss of muscle, whereas starvation initially results in the loss of fat (Morley J E et al, Am J Clin Nutr 2006; 83: 735-43).

In addition to weight loss, cachexia is also associated with fatigue, weakness, nausea, decreased performance status and psychological distress from changes in body image. Treatments used/tried include progestins, corticosteroids, metoclopramide, cannabinoids, thalidomide, melatonin, clenbuterol, anabolic steroids, omega 3 fatty acids and NSAIDs.

SUMMARY OF THE INVENTION

The present invention provides a method for treating cachexia by administering compounds that are antagonists or partial agonists of both beta-adrenergic receptors and of 5-HT1a receptors.

(S)-pindolol, (S)-propranolol, (S)-carteolol, (S)-penbutolol, (S)-alprenolol, tertatolol, (S)-tertatolol, mepindolol, (S)-mepindolol, bopindolol and (S)-bopindolol are preferred compounds for this purpose. (S)-pindolol is a particularly preferred compound.

According to the present invention, (S)-pindolol [also known as (−)-pindolol, S(−)-pindolol, S-(−)-1-(1H-indol-4-yloxy)-3-(1-methylethylamino)propan-2-ol], and (S)-propranolol [also known as (−)-propranolol, S(−)-propranolol, (S)-1-isopropylamino-3-(1-naphthyloxy)-2-propanol] which both have affinity for both beta-adrenergic receptors and 5-HT1a receptors, have beneficial effects in subjects suffering from cachexia.

It is considered that the preferred compounds produce reduced alteration in blood pressure compared with a conventional beta-blocker, which reduces blood pressure. It is also considered that the preferred compounds reduce fatigue.

DETAILED DESCRIPTION OF THE INVENTION

This invention envisages the use of any substance that interacts with both the beta-adrenoceptor and the 5-HT1a receptor as either an antagonist or a partial agonist.

Beta-adrenoceptor antagonists have been claimed to be useful in the treatment of cachexia according to EP99947762, the contents of which are included by reference. This patent refers to a method of treating weight loss due to underlying disease by the administration of an agent which reduces sympathetic nervous system activity. WO2006102476 describes combinations of beta adrenergic antagonists and anti-inflammatory agents, such as NSAIDs (non-steroidal anti-inflammatory agents). The racemic forms of pindolol and propranolol are specifically mentioned in these patents, although the utility of the enantiomers is not mentioned.

As used herein, and as would be understood by the person skilled in the art, the enantiomeric forms of racemates refer to compositions consisting substantially of a single isomer, i.e. substantially free of the other isomer, containing at least 90% of such single isomer, or preferably at least 95% of such single isomer, or more preferably at least 98% of such single isomer.

Pindolol and propranolol are used in the treatment of hypertension and angina as the racemic substances, RS pindolol and RS propranolol, due mainly to their beta-adrenergic receptor activity. The pharmacological properties of the R-form of pindolol differ from those of the S-enantiomer. In addition to an affinity for beta adrenergic receptors, (S)-pindolol also has affinity for 5-HT1a receptors in a similar dose range. It has recently been reported (WO2006030306) that (S)-pindolol produced no alteration in blood pressure in a majority of healthy subjects whereas a similar dose of racemic pindolol had the effect of reducing diastolic blood pressure. Thus, (S)-pindolol is behaving unlike a conventional beta-blocker, which reduces blood pressure.

(S)-propranolol interacts enantioselectively with the 5HT-1a receptor (J. Pharm. Pharmacol. 39, 664-666, (1987)) and functional tests have confirmed that (S)-propranolol but not (R)-propranolol blocked the suppressant effects of 5-HT1a agonists on dorsal raphe neuronal firing (Eur J Pharmacol. 1986 Sep. 9; 128 (3): 295-8). The different effects of (S)- and (R)-propranolol have also been observed in forearm blood flow experiments (J Cardiovasc Pharmacol. 1995 February; 25 (2): 268-72).

The present invention utilizes dual-acting compounds to interact with both beta-adrenergic receptors and 5-HT1a receptors and as a result to provide the means for the treatment of cachexia while avoiding a common side effect of beta-adrenergic antagonists, namely fatigue. In another aspect the invention utilizes dual-acting compounds to interact with both beta-adrenergic receptors and 5-HT1a receptors to promote weight gain, or reduce or prevent weight loss, in patients suffering from a chronic illness including but not limited to cancer, heart failure, chronic obstructive pulmonary diseases (COPD), liver failure, kidney failure, stroke, rheumatoid arthritis, severe burn injury and HIV/AIDS, while avoiding a common side effect of beta-adrenergic antagonists, namely fatigue. Both antagonists and partial agonists of these receptors are envisaged by the invention. Partial agonists of the beta-adrenergic receptor have been characterised as having intrinsic sympathomimetic activity. Preferred embodiments of the invention include the isomers (S)-pindolol, (S)-propranolol, (S)-carteolol, (S)-penbutolol or (S)-alprenolol as well as the racemic tertatolol, mepindolol or bopindolol or salts thereof. The inventions also envisages the utilisation of the S-enantiomers of tertatolol, mepindolol or bopindolol.

One of the side effects of beta-adrenoceptor antagonists is fatigue. This is a particular problem in cachexia as manifest in serious conditions such as cancer, heart failure and so on. For example, beta-adrenoceptor antagonist therapy remains substantially underused in heart failure patients despite its proven mortality benefits. Reluctance to prescribe these agents may derive from concerns about their association with symptoms of fatigue. According to Ko et al (JAMA 2002; 288: 351-7), an increase of 15% in reported symptoms of fatigue is found in heart failure patients treated with beta-adrenoceptor antagonists.

In one aspect, compounds of the invention are particularly useful in the treatment of cachexia compared to other drugs which act solely as beta-adrenergic antagonists because, for example in humans, fatigue is either not increased or in some cases may be reduced, while efficacy against cachectic weight loss is maintained. Preferably, in the subject treated, fatigue is reduced.

In another aspect, compounds of the invention are effective against cachexia in the absence of an effect on blood pressure, for example in humans, or in the subject treated. This is important in the context of cancer patients who often have autonomic nervous system dysfunction.

For cancer patients, fatigue can also be a limiting factor in the extent to which they can tolerate radio- or chemotherapy. Improving fatigue can therefore be a means of enabling more effective cancer treatment. Compounds of the invention are envisaged to be particularly beneficial in the treatment of cachectic cancer patients suffering from cancer fatigue.

Fatigue in general is a common health complaint. It is, however, one of the hardest terms to define, and a symptom of many different conditions.

U.S. Pat. No. 6,855,729 proposes (S)- and R(S)-pindolol for the treatment of fibromyalgia and related chronic fatigue syndromes. In this manifestation of fatigue, conventional diagnostic evaluation does not reveal a structural or biochemical abnormality. Attempts at elucidating the pathophysiology have produced inconsistent findings and a wide array of theories have been put forward. By comparison the fatigue found in conjunction with chronic illnesses such as heart failure, cancer, COPD, liver failure, kidney failure and AIDS represents a phenomenon at least partly associated with a well-defined abnormality.

The pathophysiological heterogeneity of the condition underpins a range of therapeutic approaches to fatigue wherein an agent that is useful in one type of fatigue is not necessarily useful in another type. Treatments for fatigue in general have included iron supplements for anemia, medications and devices to help sleep apnea, medications to control blood sugar, thyroid medications, antibiotics to control infection and vitamins.

Although fatigue is one of the most common symptoms in cancer as well as heart failure, few medications are effective in treating it in this context. Psychostimulants can give a sense of well-being, decrease fatigue, and increase appetite. However, these drugs can also cause sleeplessness, euphoria, and mood changes. High doses and long-term use may cause loss of appetite, nightmares, sleeplessness, euphoria, paranoid behaviour, and possible heart problems.

As used in this invention, the usual doses of (S)-pindolol will be in the range of 2.5 mg to 50 mg daily in single or divided doses, depending upon the therapeutic response and the pharmaceutical form. The usual doses of (S)-propranolol will be in the range of 2.5 mg to 100 mg daily in single or divided doses, depending upon the therapeutic response and the pharmaceutical form.

Various pharmaceutical presentations are possible, including (but not limited to) tablets, capsules, oral solutions and suspensions and parenteral solutions. Pharmaceutical formulations for oral use in which the active substance is released in a controlled and slower fashion such that the treatment may be administered less frequently are also included.

The invention is intended for the treatment of mammals, including humans.

The ability of the pindolol to treat gastrointestinal disease has been demonstrated in a clinical setting as described in U.S. Pat. Nos. 5,324,738 and 5,403,848.

EXAMPLE

Ascites hepatoma Yoshida AH-130 cells ($10^8$ cells) are inoculated into 180-200 g male Wistar rats. Alternatively animals receive saline injection only (sham). The animals are housed in groups of three. The day after inoculation animals are randomized into various groups and then receive twice daily treatment with either placebo or compounds over a period of up to 17 days. The primary endpoints of the study include assessment of body weight, body composition (with and without tumour) and survival. Organ weight is assessed at the end of the study (or after death) as a secondary endpoint. In addition locomotor activity is used to assess fatigue using Supermex system (Muromachi, Tokyo, Japan) over a period of 24 hours in cages where the animals are placed individually (type 3 cage); missing data (if due to death) are imputed as 'zero' activity; a sensitivity analysis without imputed points is additionally performed. Food intake is also measured.

Results are expressed as mean±SEM at the end of the study except where stated otherwise. Doses represent total daily dose given by oral gavage.

|  | Placebo | Bisoprolol 5 mg/kg/d | Bisoprolol 50 mg/kg/d | S-pindolol 0.3 mg/kg/d | S-pindolol 3 mg/kg/d |
| --- | --- | --- | --- | --- | --- |
| n | 24 | 14 | 14 | 10 | 10 |
| Body weight without tumour (g) | 167.92 ± 8.05 | 202.0 ± 16.04 | 159.18 ± 9.64 | 178.89 ± 17.04 | 215.10 ± 19.89 |
| Weight gain without tumour (g) | −26.46 ± 7.72 | −5.46 ± 15.95 | −30.30 ± 10.95 | −8.50 ± 19.19 | 17.30 ± 20.08 |
| Lean tissue without tumour (g) | 132.32 ± 6.27 | 158.10 ± 11.86 | 124.77 ± 7.17 | 152.37 ± 15.47 | 171.99 ± 15.92 |
| Lean tissue gain without tumour (g) | −18.45 ± 6.11 | −1.38 ± 11.31 | −28.96 ± 6.64 | −1.17 ± 15.84 | 18.90 ± 16.06 |
| Food intake day 11 (g) | 7.83 ± 1.28 | 16.00 ± 3.07 | 9.94 ± 2.10 | 7.75 ± 5.22 | 15.33 ± 3.84 |
| Locomotor activity 24 h day 11 | 320 ± 46 | 315 ± 58 | 277 ± 39 | 361 ± 38 | 368 ± 50 |

The results clearly show that S-pindolol is able to reduce cachectic weight loss in an animal model of cancer cachexia while having a positive effect on locomotor activity, as a marker for fatigue, and also reducing the tumour weight. By comparison, a standard beta-adrenergic receptor blocker bisoprolol is neutral to negative with respect to locomotor activity.

The invention claimed is:

1. A method of treating cachexia in a mammal comprising administering to the mammal a composition comprising (S)-pindolol or a salt thereof as the sole active agent or.

2. The method of claim 1 wherein the compound does not have an effect on blood pressure.

3. The method of claim 1 wherein the cachexia is due to ageing.

4. The method of claim 1 wherein the cachexia is due to cancer.

5. The method of claim 1 wherein the cachexia is due to heart failure.

6. The method of claim 1 wherein the cachexia is due to COPD.

7. The method of claim 1 wherein the cachexia is due to liver failure or cirrhosis.

8. The method of claim 1 wherein the cachexia is due to stroke.

9. The method of claim 1 wherein the cachexia is due to rheumatoid arthritis.

10. The method of claim 1 wherein the cachexia is due to severe burn injury.

11. The method of claim 1 wherein the cachexia is due to kidney failure.

12. The method of claim 1 wherein the cachexia is due to HIV/AIDS.

13. The method of claim 1 wherein the cachexia is found in the absence of a diagnosed chronic illness.

14. The method of claim 1 wherein the method of treating does not reduce the mammal's blood pressure.

15. The method of claim 14 wherein the mammal is a human being.

16. A method of treating cachexia in a mammal, comprising administering to the mammal a composition comprising (S)-pindolol, wherein the composition is substantially free of (R)-pindolol.

* * * * *

UNITED STATES PATENT AND TRADEMARK OFFICE
CERTIFICATE OF CORRECTION

PATENT NO.        : 8,716,325 B2                                        Page 1 of 1
APPLICATION NO.   : 12/312756
DATED             : May 6, 2014
INVENTOR(S)       : David Cavalla It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 974 days.

Signed and Sealed this

Twenty-ninth Day of September, 2015

Michelle K. Lee
*Director of the United States Patent and Trademark Office*